US00PP23107P2

(12) United States Plant Patent
Ferguson et al.

(10) Patent No.: US PP23,107 P2
(45) Date of Patent: Oct. 16, 2012

(54) STRAWBERRY PLANT NAMED 'DRISSTRAWEIGHTEEN'

(50) Latin Name: *Fragaria×ananassa*
Varietal Denomination: DrisStrawEighteen

(75) Inventors: Michael D. Ferguson, Moorpark, CA (US); Terrance C. Moran, Ojai, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/134,820

(22) Filed: Jun. 17, 2011

(51) Int. Cl.
*A01H 5/00* (2006.01)

(52) U.S. Cl. ..... Plt./209

(58) Field of Classification Search ..... Plt./209
See application file for complete search history.

*Primary Examiner* — Annette Para
(74) *Attorney, Agent, or Firm* — Jondle & Associates, P.C.

(57) ABSTRACT

A new and distinct variety of strawberry plant named 'DrisStrawEighteen'; characterized by having medium sized, conically-shaped berries that are dark red and strongly sweet, is disclosed.

3 Drawing Sheets

Genus and species: *Fragaria×ananassa.*
Variety denomination: 'DrisStrawEighteen'.

BACKGROUND OF THE NEW PLANT

The present invention relates to a new and distinct strawberry variety designated 'DrisStrawEighteen' and botanically known as *Fragaria×ananassa*. This new strawberry variety was the result of a controlled cross conducted in Ventura County, Calif. in 2004 between the proprietary female parent '91J302' (unpatented) and the proprietary male parent '26H165' (unpatented). A single plant was selected for asexual propagation via tissue culture and vegetative cuttings in Shasta County, Calif. in 2005.

'DrisStrawEighteen' underwent further testing in Ventura County, Calif. for five years (2005-2010). The present invention has been found to retain its distinctive characteristics through several asexual propagations via stolons.

Plant Breeder's Rights for this variety have not been applied for. 'DrisStrawEighteen' has not been made publicly available or sold more than one year prior to the filing date of this application.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from eight-month-old plants.

DESCRIPTION OF THE NEW VARIETY

Figure 1:
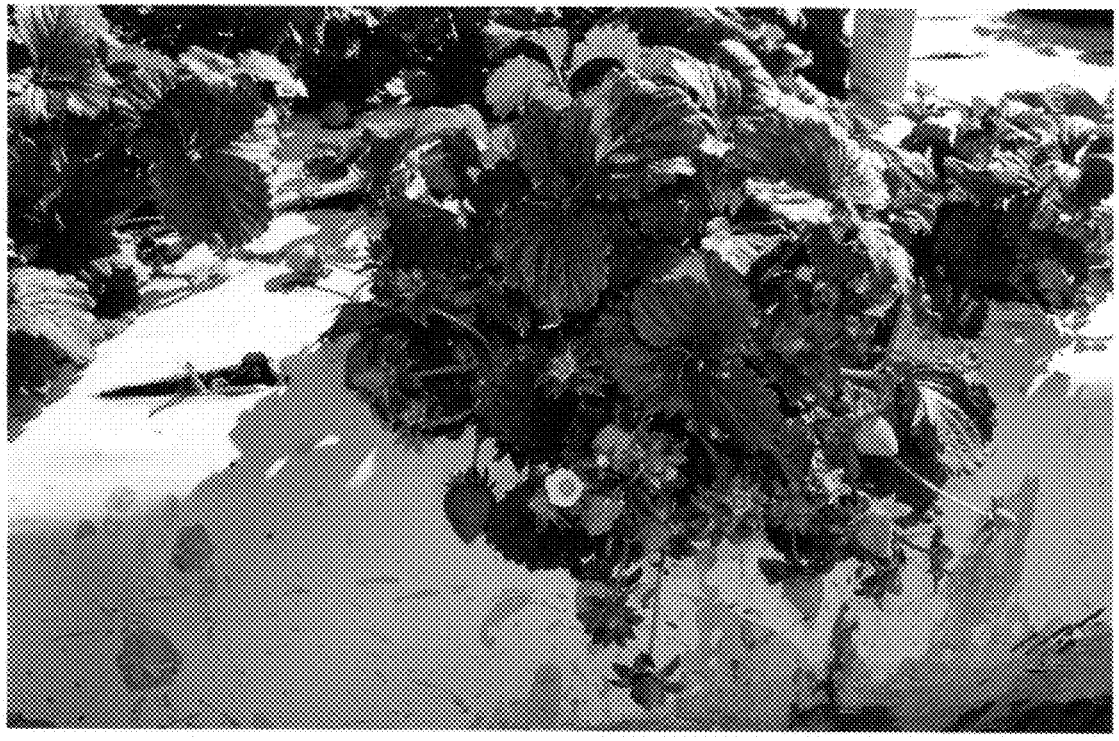
FIG. 1 shows overall plant habit including fruit at various stages of development.
Figure 2:
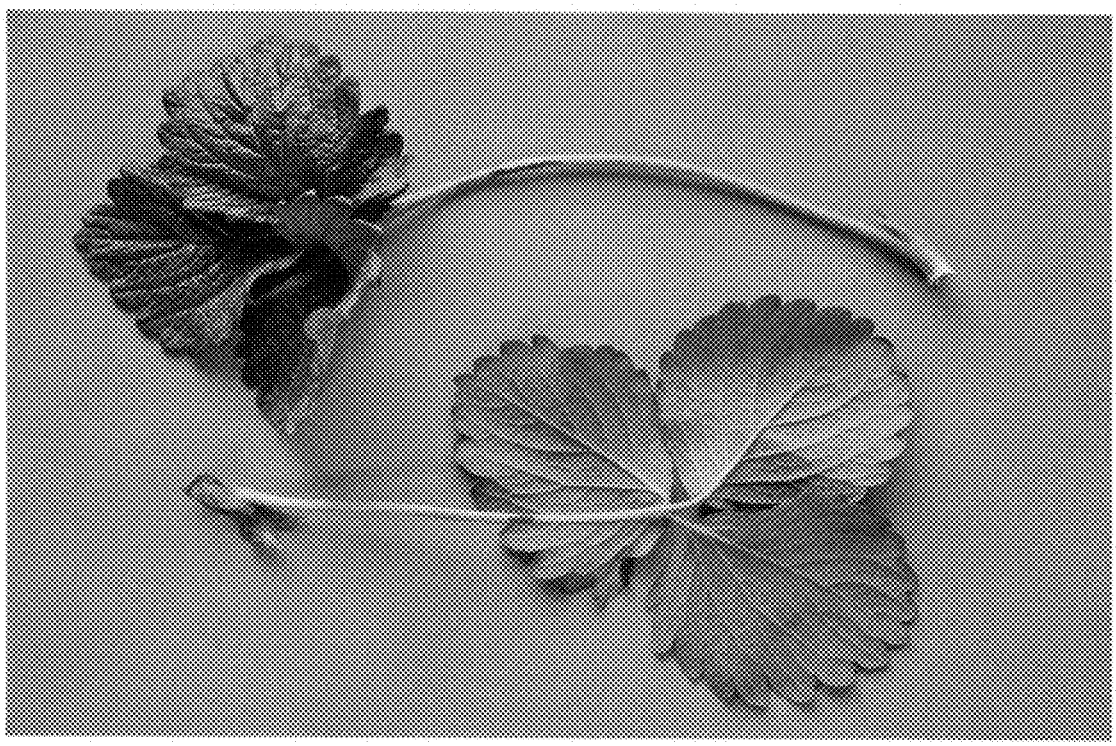
FIG. 2 shows leaves of the plant with three leaflets.
Figure 3:
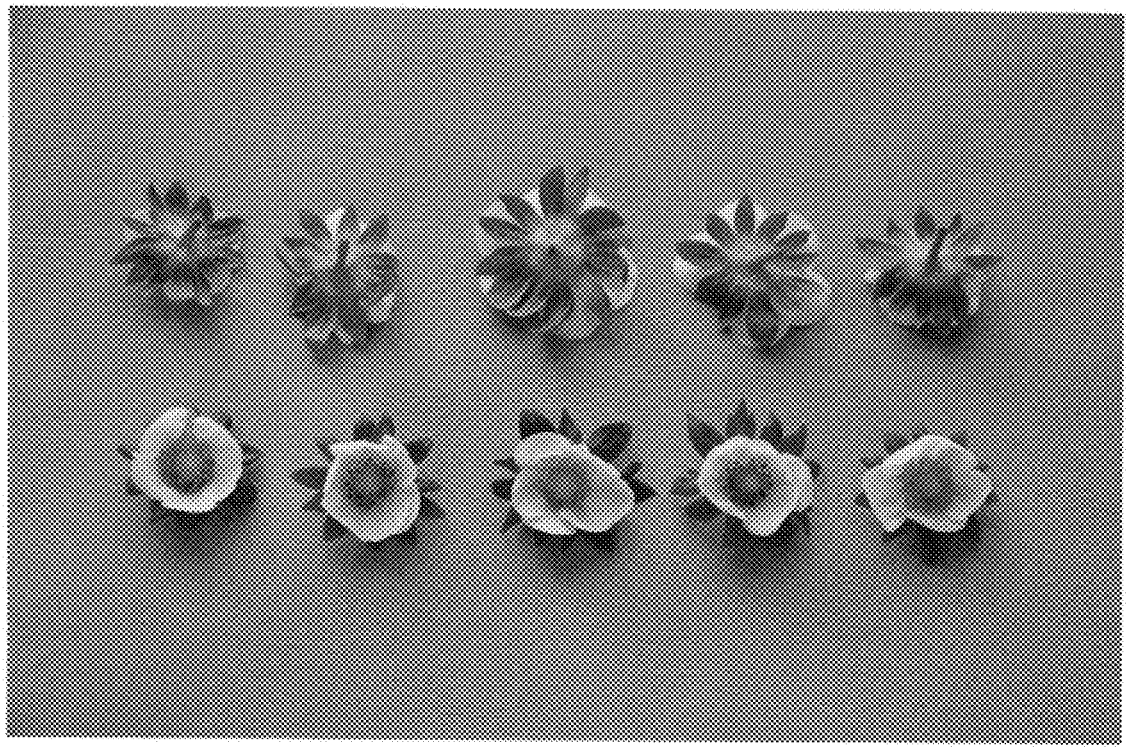
FIG. 3 shows both the upper surface and lower surface of several of the flowers.
Figure 4:
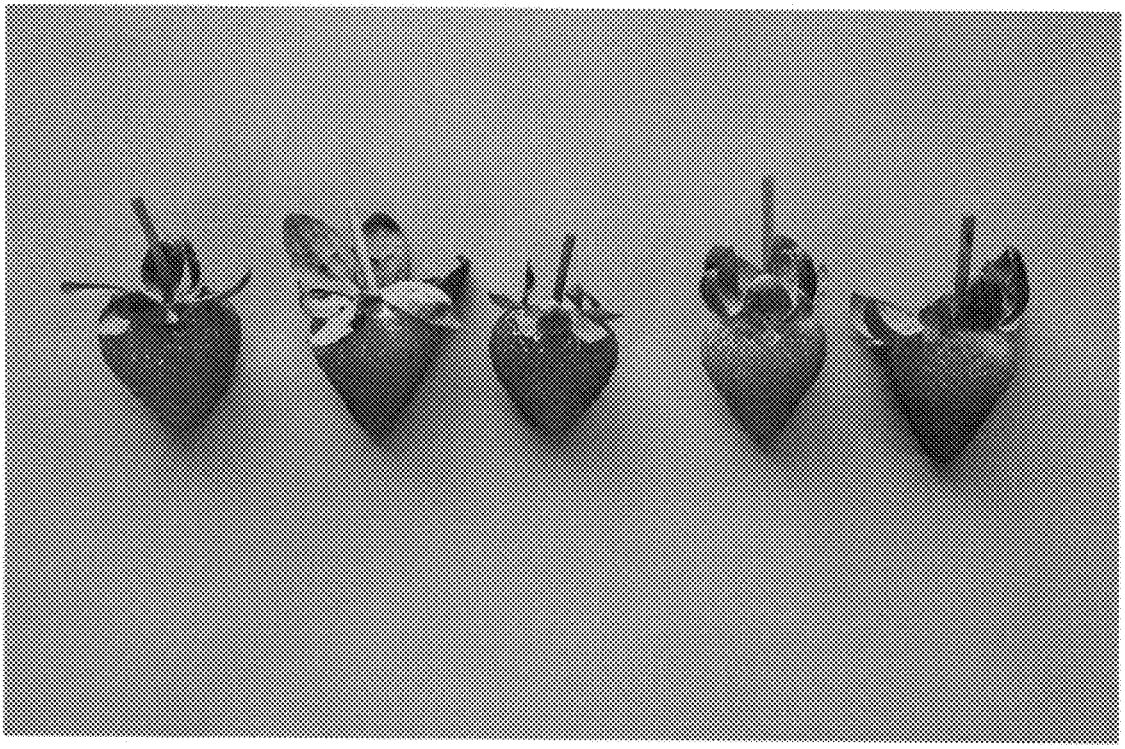
FIG. 4 shows the whole fruit.
Figure 5:
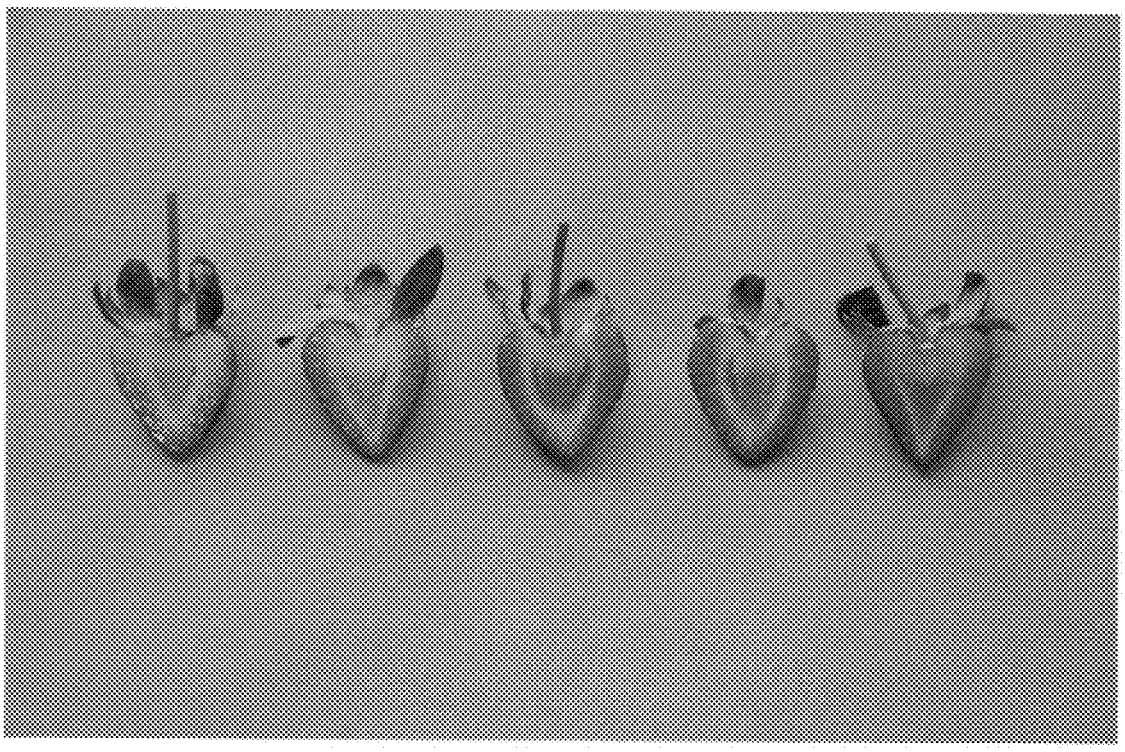
FIG. 5 shows the fruit in longitudinal cross-section.

The following detailed descriptions set forth the distinctive characteristics of 'DrisStrawEighteen'. The data which define these characteristics is based on observations taken in Ventura County, Calif. from 2005 to 2010. This description is in accordance with UPOV terminology. Color designations, color descriptions, and other phenotypical descriptions may deviate from the stated values and descriptions depending upon variation in environmental, seasonal, climatic, and cultural conditions. 'DrisStrawEighteen' has not been observed under all possible environmental conditions. The botanical description of 'DrisStrawEighteen' was taken from eight-month-old plants. Color terminology follows The Royal Horticultural Society Colour Chart, London (R.H.S.) (2001).

DETAILED BOTANICAL DESCRIPTION OF THE PLANT

Classification:
- *Species.*—*Fragaria×ananassa.*
- *Common name.*—Strawberry.
- *Denomination.*—'DrisStrawEighteen'.

Parentage:
- *Female parent.*—The proprietary variety '91J302' (unpatented).
- *Male parent.*—The proprietary variety '26H165' (unpatented).

Plant:
- *Height.*—27.2 cm.
- *Diameter.*—42.0 cm.
- *Number of crowns/plant.*—3.
- *Habit.*—Globose and semi-upright.
- *Density of individual plant.*—Medium.
- *Vigor.*—Medium.

Leaves:
- *Terminal leaflet length.*—7.8 cm.
- *Terminal leaflet width.*—7.4 cm.
- *Terminal leaflet length/width ratio.*—1.1.
- *Number of teeth/terminal leaflet.*—17.
- *Shape of teeth.*—Crenate.
- *Color.*—Upper surface: RHS 137A (Dark green). Lower surface: RHS 148B (Medium Yellow-green).
- *Leaf shape in cross section.*—Slightly concave.
- *Leaf blistering.*—Medium.
- *Leaf glossiness.*—Medium.

*Number of leaflets.*—3 only.
*Terminal leaflet margin profile.*—Revolute (margins rolled backwards).
*Terminal leaflet length/width ratio.*—As long as broad (1:1).
*Terminal leaflet shape.*—Orbicular.
*Terminal leaflet base shape.*—Obtuse.
*Terminal leaflet apex shape.*—Convex.

Petiole:
*Length.*—17.4 cm.
*Diameter.*—2.66 mm.
*Pubescence.*—Sparse.
*Pose of hairs.*—Downwards.
*Color.*—RHS 145A (Medium Yellow-green).

Petiolule:
*Color.*—RHS 144B (Medium Yellow-green).
*Length.*—1.98 mm.
*Diameter.*—1.48 mm.

Stipule:
*Length.*—3.2 cm.
*Width.*—9.11 mm.
*Pubescence.*—Medium.
*Stipule anthocyanin coloration.*—Absent or very weak.

Stolon:
*Number.*—Few.
*Average number of daughter plants per plant.*—12.
*Stolon anthocyanin.*—RHS 42A (Medium red).
*Thickness.*—Medium.
*Pubescence.*—Medium.

Inflorescence:
*Position relative to foliage.*—Beneath.
*Number of flowers.*—Medium.
*Time of flowering* (50% *of plants at first flower*).—Early.
*Flower size.*—Medium.
*Diameter.*—2.602 cm.
*Petals.*—Shape: Orbicular. Apex: Rounded. Base: Concave-convex. Margin: Entire. Spacing: Overlapping. Length: 1.487 cm. Width: 1.457 cm. Length/width ratio: 1.0; as long as broad. Typical and observed petal number per flower: 6. Color (Both surfaces): RHS 155D (White).
*Calyx.*—Diameter: 3.428 cm. Diameter relative to corolla: Larger. Inner calyx diameter relative to outer: Same size.
*Sepal.*—Shape: Elliptical. Apex: Truncate. Margin: Entire. Length: 1.278 cm. Width: 6.14 mm. Typical and observed sepal number per flower: 11. Color: RHS 1A (Medium Green-yellow).
*Receptacle color.*—RHS 1A (Medium Green-yellow).
*Anther color.*—RHS 14A (Medium Yellow-orange).

Fruiting truss:
*Length.*—23.1 cm; long.
*Diameter at base of truss.*—5.11 mm.
*Number of berries per fruiting truss.*—3.
*Attitude at first picking.*—Prostrate.
*Color at base of truss.*—RHS 144A (Medium Yellow-green).

Fruit:
*Length.*—4.141 cm.
*Width.*—3.783 cm.
*Length/width ratio.*—1.1.
*Fruit hollow length.*—1.281 cm.
*Fruit hollow width.*—1.072 cm.
*Fruit hollow length/width ration.*—1.2.
*Fruit hollow center* (*size*).—Small.
*Weight* (*per individual berry*).—27.2 g.
*Fruit ratio of length/maximum width.*—As long as broad.
*Relative fruit size.*—Medium.
*Predominant fruit shape.*—Conical.
*Difference in shape between primary and secondary fruits.*—None or very slight.
*Unevenness of fruit surface.*—Even or very slightly uneven.
*Fruit skin color.*—RHS 46B (Dark red).
*Evenness of fruit color.*—Even or very slightly uneven.
*Fruit glossiness.*—Medium.
*Insertion of achenes.*—Below surface.
*Achene coloration* (*sunward side of berry*).—RHS 185B (Dark Greyed-purple).
*Achene coloration* (*shaded side of berry*).—RHS 153C (Medium Yellow-green).
*Achenes per berry.*—253.
*Band without achenes.*—Absent or very narrow.
*Insertion of calyx.*—Level.
*Pose of calyx segments.*—Spreading — outwards to reflexed — upwards.
*Size of calyx in relation to fruit.*—Much larger.
*Adherence of calyx.*—Strong.
*Firmness of flesh.*—Firm.
*Color of flesh* (*excluding core*).—RHS N34B (Medium orange-red).
*Color of core.*—RHS 155C (White).
*Evenness of flesh color.*—Uneven.
*Distribution of flesh color.*—Marginal and central.
*Sweetness.*—Strong.
*Acidity.*—Medium.
*Texture when tasted.*—Fine.
*Type of bearing.*—Fully everbearing — fully remontant.
*Grams of fruit/plant.*—335.2 g.
*Harvest interval.*—Early September to mid-October.
*Harvest maturity.*—Early.

Disease, pest, and stress resistance:
*Botrytis fruit rot.*—Susceptible.
*Powdery mildew.*—Moderately susceptible.
*Verticillium wilt.*—Susceptible.
*Leather Rot.*—Moderately susceptible.
*Red stele.*—Susceptible.
*Leaf spots* (*Ramularia tulasnei*).—Moderately susceptible.
*Leaf scorch.*—Moderately susceptible.
*Leaf blight.*—Moderately susceptible.
*Black root rot.*—Moderately susceptible.
*Xanthomonas fragariae.*—Moderately susceptible.
*Tetranychus urticae.*—Moderately susceptible.
*Tarsonemus pallidus.*—Moderately susceptible.
*Aphelencoides fragariae.*—Moderately susceptible.
*Pratylenchus penetrans.*—Moderately susceptible.
*Ditylenchus dipsac.*—Moderately susceptible.
*Anthonomus rubi.*—Moderately susceptible.
*Aphis spp.* (*Aphids*).—Moderately susceptible.
*Lygus hesperus* (*Lygus bug*).—Susceptible.
*Drought.*—Susceptible.
*High temperatures.*—Moderately susceptible.
*Wind.*—Moderately resistant.

*High pH*.—Moderately resistant.
*High soil salt levels*.—Susceptible.
*Water logging*.—Moderately susceptible.

COMPARISON WITH PARENTAL AND COMMERCIAL VARIETIES

When 'DrisStrawEighteen' is compared to the proprietary female parent '91J302' (unpatented), 'DrisStrawEighteen' has a more vigorous growth habit, higher yields, improved fruit firmness, and improved nursery propagation performance than '91J302'.

When 'DrisStrawEighteen' is compared to the proprietary male parent '26H165' (unpatented), 'DrisStrawEighteen' has a more vigorous growth habit, has higher yields, better flavor, improved fruit appearance, and better shelf-life than '26H165'.

When 'DrisStrawEighteen' is compared to the commercial variety 'DrisStrawThree' (U.S. Plant Pat. No. 19,673), the petiole pose of hairs for 'DrisStrawEighteen' is downwards, while the petiole pose of hairs for 'DrisStrawThree' is outwards to downwards. In addition, 'DrisStrawEighteen' has a conical shape, and a fine texture when tasted, while 'DrisStrawThree' has a cylindrical shape, and a very fine texture when tasted.

When 'DrisStrawEighteen' is compared to the commercial variety 'DrisStrawSeventeen' (unpatented), the fruit of 'DrisStrawEighteen' has a conical shape while the shape of 'DrisStrawSeventeen' is wedged. In addition, 'DrisStrawEighteen' has fruit with strong sweetness and a fine texture when tasted, while 'DrisStrawSeventeen' has fruit with medium sweetness and coarse texture when tasted.

We claim:

1. A new and distinct variety of strawberry plant as described and shown herein.

* * * * *